United States Patent [19]

Quinn

[11] 4,447,236
[45] May 8, 1984

[54] INFUSION CATHETER SYSTEM

[75] Inventor: David R. Quinn, Pembroke Pines, Fla.

[73] Assignee: Cordis Corporation, Miami, Fla.

[21] Appl. No.: 346,345

[22] Filed: Feb. 5, 1982

[51] Int. Cl.³ .............................................. A61M 5/00
[52] U.S. Cl. .................................... 604/169; 604/174; 604/248; 604/283
[58] Field of Search ............................. 128/656–658, 128/DIG. 6, DIG. 26; 604/53, 169, 174, 177, 246, 248, 280, 283, 93, 158, 161, 167, 178, 256

[56] References Cited

U.S. PATENT DOCUMENTS

| | | | |
|---|---|---|---|
| 3,485,234 | 12/1969 | Stevens | 128/657 |
| 3,812,851 | 5/1974 | Rodriguez | 128/DIG. 6 |
| 3,934,576 | 1/1976 | Danielsson | 604/169 X |
| 3,977,400 | 8/1976 | Moorehead | |
| 4,000,739 | 1/1977 | Stevens | 128/656 X |
| 4,072,146 | 2/1978 | Howes | |
| 4,089,337 | 5/1978 | Kronner | 128/656 X |
| 4,144,884 | 3/1979 | Tersteegen et al. | |
| 4,149,535 | 4/1979 | Volder | |
| 4,202,332 | 5/1980 | Tersteegen et al. | |
| 4,235,232 | 11/1980 | Spaven et al. | |
| 4,299,226 | 11/1981 | Banka | 128/657 X |

Primary Examiner—C. Fred Rosenbaum
Assistant Examiner—Michelle N. Lester
Attorney, Agent, or Firm—Henry W. Collins; Thomas R. Vigil

[57] ABSTRACT

An infusion catheter system which includes a generally cylindrical housing member having a passageway extending therethrough, a guiding catheter having a proximal end disposed at one end of the cylindrical housing member such that the passageway in the housing member communicates with a passage in the guiding catheter, and an infusion catheter slidably positioned within the passage of the guiding catheter. The catheter system also includes a manifold valve which is coupled to the housing member for applying a first fluid through the housing member to the passage of the guiding catheter, and a second manifold valve which is coupled to the infusion catheter for applying a second fluid through the passage of the infusion catheter. Typically, an anticoagulate fluid is applied through the guiding catheter to prevent blood clotting during an infusion procedure and a blood clot dissolving fluid, such as streptokinase, is applied through the infusion catheter. With this catheter infusion system, the distal end of the infusion catheter may be precisely positioned within an artery so that the clot dissolving fluid may be effectively administered.

6 Claims, 5 Drawing Figures

INFUSION CATHETER SYSTEM

BACKGROUND OF THE INVENTION

This invention relates to infusion catheters, and particularly those used to infuse a drug directly into the arterial system of the human body.

The use of catheters in the diagnosis of diseases of various organs within the human body is well known. In recent years catheters have been used to carry out interventional therapy within the vascular system of the human body. More particularly, catheters have been used to infuse certain enzymes into coronary arteries to dissolve blood clots which have formed in these arteries.

In the past, attempts have been made to improve the blood supply to the heart by surgically opening an obstructed coronary vessel, by transplanting a peripheral artery into the heart muscle, or by stimulating the pericardial capillaries to grow into the myocardium. These treatment techniques have been shown to be of value in alleviating certain diseases of the heart, however, certain risks are involved with these procedures.

Recently, certain enzymatic drugs, such as streptokinase, have been infused directly into the coronary arteries in an attempt to dissolve blood clots before the heart is permanently damaged by such clots. In this procedure, a catheter is inserted through the femoral artery in the groin, up through the aorta into the coronary arteries that provide blood to the heart. A radiopaque dye is injected through the catheter so that blood clots which have formed in these arteries may be observed by fluoroscopy. The distal tip of an infusion catheter is then moved into proximity with the blood clot, and a selected enzyme, for example streptokinase, is infused into the vicinity of the blood clot in order to dissolve the clot.

The technique of dissolving the blood clots by infusion of a selected enzyme is described in more detail in an article entitled, "Segmental Perfusion of the Coronary Arteries with Fibrinolysin in Man Following a Myocardial Infarction" by Robert J. Boucek, M.D., et al, *The American Journal of Cardiology*, August, 1960.

SUMMARY OF THE INVENTION

In accordance with the present invention, there is provided an infusion catheter system which includes an elongated housing member having a passageway extending therethrough, a guiding catheter coupled to one of the ends of the housing member such that the passageway of the housing member communicates with a passage in the guiding catheter. A small diameter infusion catheter is slidably positioned within the passage of the guiding catheter. The infusion catheter has a distal end which extends for a short distance beyond the end of the guiding catheter. The infusion catheter system also includes a first manifold valve which is coupled to the elongated housing member for applying a fluid through the housing member to the guiding catheter, and a second manifold valve which is coupled to the infusion catheter for applying another fluid, such as a blood clot dissolving enzyme, to the infusion catheter. With this arrangement, it is possible to position the guiding catheter within a blood vessel so that the distal end of this catheter is in the general vicinity of a blood clot to be removed, and then slide the infusion catheter within the guiding catheter so that the distal end of the infusion catheter is placed in a very precise location relative to the blood clot. One of the manifold valves is used to direct a fluid, such as heparin, through the guiding catheter in order to prevent clotting of the blood, and the other manifold valve is utilized to apply an infusion fluid, such as the clot dissolving enzyme.

In another embodiment of the present invention, the manifold valves each include a group of three separate valves so that other fluids, such as a radiopaque dye or saline solution, may be infused into either the guiding catheter or the infusion catheter. The radiopaque dye is employed to determine the exact location of the distal end of the catheter through fluoroscopic inspection.

In still another embodiment of the present invention, the housing member also includes a hemostasis valve positioned at the other end of the housing member and the infusion catheter extends through the hemostasis valve, through the passageway of the housing member and then through the passage of the guiding catheter. The hemostasis valve serves to provide a fluid-tight seal between the housing member and the infusion catheter while allowing the catheter to be moved relative to the housing member and the guiding catheter.

In still another embodiment of the present invention, the infusion catheter includes a hemostasis valve positioned at the proximal end of this catheter to allow a guidewire to be inserted through the infusion catheter while maintaining a fluid-tight seal between the guidewire and the infusion catheter.

Other advantages and features will become apparent to those skilled in the art from the following description of a preferred embodiment of the invention taken with the accompanying drawings.

DESCRIPTION OF A PREFERRED EMBODIMENT

Figure 1:
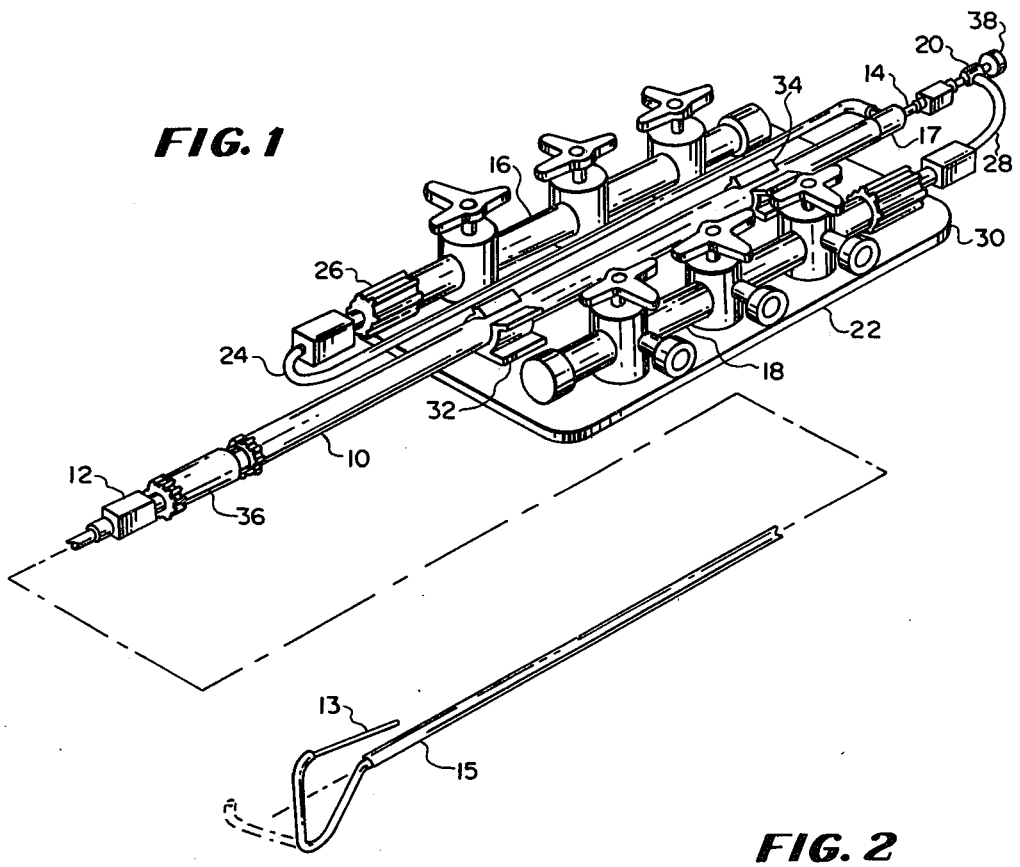
FIG. 1 is an oblique elevational view of one embodiment of the infusion catheter system of the present invention.
Figure 2:
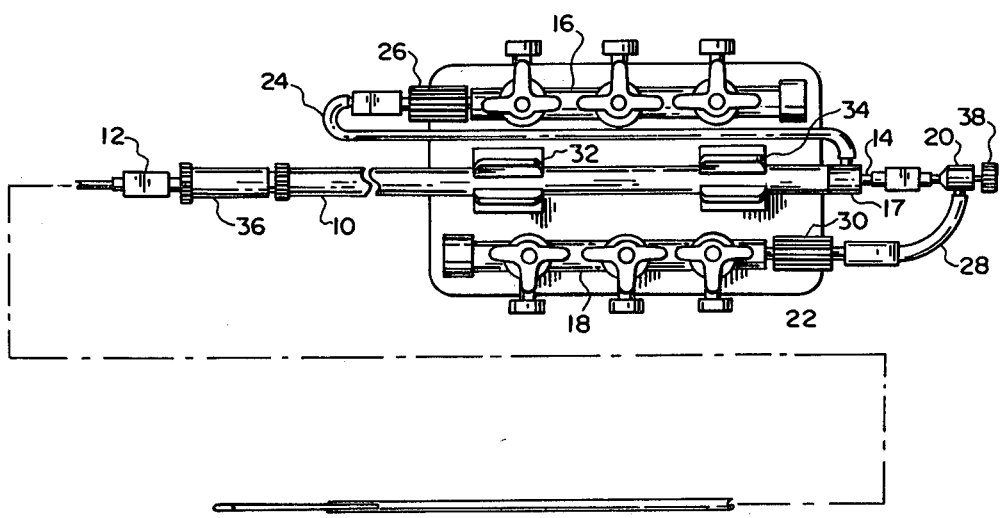
FIG. 2 is a top elevational view of the embodiment of the invention shown in FIG. 1.

As illustrated in FIGS. 1 and 2, the infusion catheter system generally comprises an elongated housing member 10 having a passageway extending through the length thereof, a guiding catheter 12 having a proximal end coupled to one end of the housing member 10, and an infusion catheter 14 which extends through the passageway of the housing member 10 and through a passage in the guiding catheter 12. As is illustrated, the infusion catheter 14 is of a length such that a distal portion 13 of the infusion catheter 14 extends beyond the end of a distal end 15 of the guiding catheter 12.

A three-valve manifold assembly 16 is coupled to the passageway of the housing member 10 so that a selected one of three fluids may be directed through this passageway to the passage of the guiding catheter 12. Another three-valve manifold assembly 18 is coupled through a hemostasis valve 20 to the infusion catheter 14 so that a selected one of three fluids may be directed to the infusion catheter 14. Both of the manifold assemblies 16, 18, and the elongated housing member 10 are mounted on a flat plate member 22 in order to retain these elements in a fixed position relative to each other.

More particularly, the guiding catheter 12 takes the form of either a right or a left femoral coronary French 7 catheter which serves the function of guiding the infusion catheter to a desired site within the human body. The manifold assemblies 16, 18 each includes three valves each of which includes an inlet port. The inlet ports are adapted to be coupled to a service of fluid such as a contrast media, a flushing solution, or any other desired solution. The manifold assembly 16 is coupled to a transfer line 24 by use of a Luer connector 26. The transfer line 24 is coupled to the port of the hemostasis valve 17 which is mounted on the end of the elongated housing member 10. The hemostasis valve 17 preferably takes the form of the device disclosed in U.S. Pat. No. 4,000,739 to Robert C. Stevens, issued Jan. 4, 1977, and assigned to the assignee of the present invention. The manifold assembly 18 is similarly coupled to a transfer line 28 through a Luer connector 30. The transfer line 28 is in turn connected to the port of the hemostasis valve 20 which is mounted on the end of the infusion catheter 14. The manifold assemblies 16, 18 are adhesively bonded to the flat plate member 22, and the housing member 10 is mounted on the plate member 22 by the use of two spring clips 32, 34.

As is illustrated, the elongated housing member 10 is coupled through a rotating adaptor 36 to the guiding catheter 12 so that the guiding catheter may be rotated relative to the housing member 10 during insertion of the catheter within the vascular system of the human body. The infusion catheter 14 takes the form of a French 3.5 catheter. The infusion catheter 14 with the associated hemostasis valve 20, is arranged to receive a stylet 38 which serves to strengthen and add stiffness to the infusion catheter 14 during the insertion of this catheter.

Figure 3:
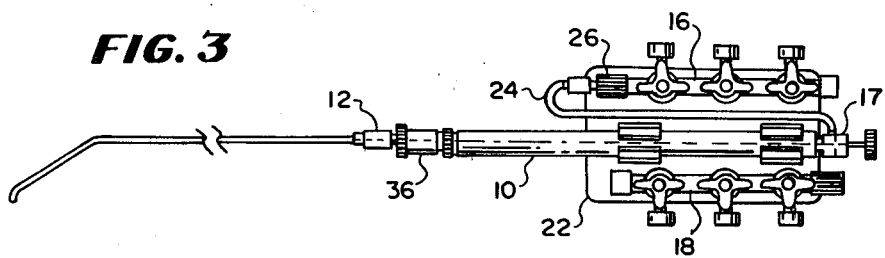
FIG. 3 is a top elevational view of the embodiment shown in FIG. 2 prior to insertion of the infusion catheter.

The operation of the infusion catheter system will be described with reference to FIGS. 3, 4 and 5. More particularly, the guiding catheter 12 is attached to the rotating adaptor 36 and a tip straightener of stylet 38 is inserted through the hemostasis valve 17 and into the guiding catheter 12 in order to generally straighten the catheter 12 as shown in FIG. 3. The manifold assembly 16 housing member 10 and guiding catheter 12 are then purged of all air by coupling a source of saline to one of the inlet ports on the manifold assembly 16 and by opening the appropriate valve in order to allow the saline solution to flow through the system.

An entry path is then established in a femoral artery of the body and the guiding catheter is inserted into the body and moved to a position so that the distal end is in the general vicinity of the arterial orifice of the artery having a clot to be dissolved. During the insertion of the catheter, a heparin solution source is coupled to one of the ports of the manifold assembly 16 and is allowed to flow through the catheter system. The plate member 22 is then secured to a drape material which covers the outside of the body in order to retain the guiding catheter in the desired position.

Figure 4:
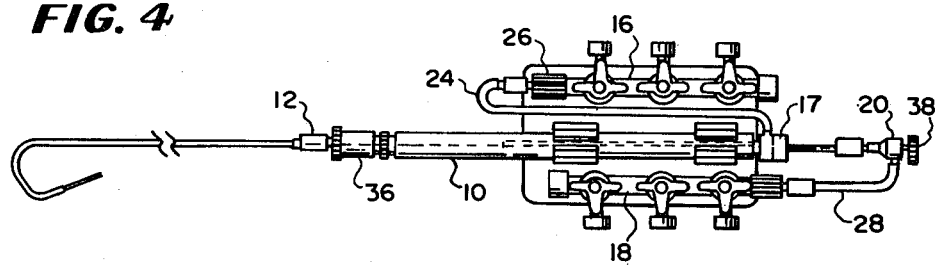
FIG. 4 is a top elevational view of the embodiment illustrated in FIG. 3 with the infusion catheter partially inserted into the catheter system; and, FIG. 5 is a top elevational view of the embodiment shown in FIG. 4 with the infusion catheter completely inserted into the catheter system.

The tip straightener is then withdrawn from the housing member 10 and the infusion catheter 14 is inserted through the hemostasis valve 17, through the housing member 10 and through the guiding catheter 12 as illustrated in FIG. 4. The stylet 38 is positioned within the infusion catheter 14 during this procedure. The infusion catheter is then advanced to a desired position. During the insertion of the infusion catheter, a heparinized saline drip is maintained through the manifold assembly 18 and through the infusion catheter 12.

Figure 5:
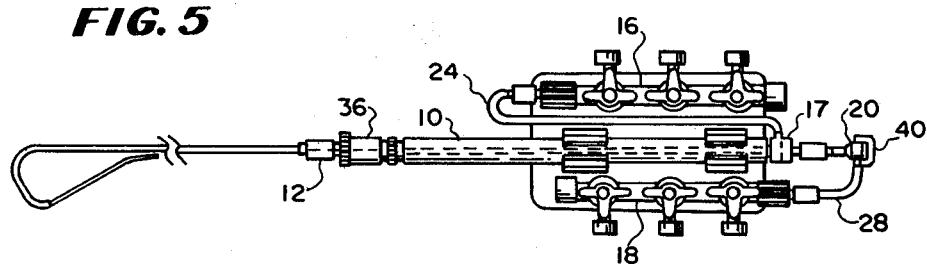

The stylet 38 is then removed from the infusion catheter 12 and a cap 40, as illustrated in FIG. 5, is placed over the end of the hemostasis valve 20 on the infusion catheter 12. When the cap 40 has been put into place, the desired enzyme for dissolving a blood clot is then coupled through one of the ports of the manifold assembly 18, the appropriate valve is opened, and the fluid is then allowed to pass into the port of the hemostasis valve 20 of the infusion catheter 14.

With the structural arrangement of the present invention, it is possible to very precisely position an infusion catheter by use of a guiding catheter. When the infusion catheter has been properly positioned, an enzyme for dissolving blood clots may then be precisely infused into the region of the blood clot to dissolve the clot.

The present invention, therefore, provides a novel infusion catheter system which is capable of providing improved infusion of various therapeutic and/or angiographic agents. Multiple injection of agents are also possible with the catheter system of the present invention. As is apparent, various modifications of the embodiment as described are possible within the scope of the invention.

What is claimed is:

1. An infusion catheter system comprising: an elongate tubular housing member having a passageway extending therethrough; a first, guiding catheter having proximal and distal ends and having a passage extending therethrough, the proximal end of said first catheter being coupled to said housing member such that the passage of said first catheter communicates with the passageway in said housing member and the distal end being adapted to be inserted into an artery or vein; a second, infusion catheter having a passage extending therethrough and being movably positioned within the passage of said first catheter and having proximal and distal ends which extend beyond the proximal and distal ends respectively of the first catheter; first fluid delivery means including first valve means coupled to said housing member for supplying a first fluid through the passage of said first, guiding catheter; and, second fluid delivery means including second valve means coupled to the proximal end of said second catheter for supplying a second fluid through the passage of said second catheter for infusion through an opening in the distal end of said second infusion catheter into an artery or vein.

2. An infusion catheter system as defined in claim 1 wherein said first valve means includes first and second valves to permit selective infusion of either a first or a second fluid through the passage of said first catheter.

3. An infusion catheter system as defined in claim 2 wherein said second valve means includes first and second valves to permit selective infusion of either a first or a second fluid through the passage of said second catheter.

4. An infusion catheter system as defined in claim 1 including a flat plate member, said tubular housing member being mounted on said plate member in the middle thereof and said first and second fluid delivery means being mounted on said plate member on opposite sides of said tubular housing member.

5. An infusion catheter system as defined in claim 4 including first and second spring clips mounted on and in the middle of said plate member and being adapted to receive and hold said tubular housing member on and to said plate member in a releasable manner.

6. An infusion catheter system as defined in claim 1 wherein said first and second fluid delivery means each include an elongate manifold having at least one fluid coupling and said respective first or second valve means being associated with said at least one fluid coupling.

* * * * *

UNITED STATES PATENT AND TRADEMARK OFFICE
CERTIFICATE OF CORRECTION

PATENT NO. : 4,447,236

DATED : May 8, 1984

INVENTOR(S) : DAVID R. QUINN (page 1 of 3)

It is certified that error appears in the above-identified patent and that said Letters Patent is hereby corrected as shown below:

Column 4, line 31, after "system" there should have been inserted -- for supplying clot inhibiting fluid and for supplying a clot dissolving enzyme to the location of a clot in a blood vessel --.

Column 4, line 32, after "having" there should have been inserted -- proximal and distal ends and --.

Column 4, line 36, after "said" there should have been inserted -- distal end of said --.

Column 4, line 45, after "including" there should have been inserted -- a first manifold having --.

Column 4, line 45, after "means", "coupled" should have been -- and a first conduit coupling of said first manifold --.

Column 4, line 45, after "fluid" there should have been inserted --, such as a clot inhibiting fluid, --.

UNITED STATES PATENT AND TRADEMARK OFFICE
CERTIFICATE OF CORRECTION

PATENT NO. :   4,447,236

DATED      :   May 8, 1984                    (page 2 of 3)

INVENTOR(S) :  DAVID R. QUINN

It is certified that error appears in the above-identified patent and that said Letters Patent is hereby corrected as shown below:

Column 4, line 47, after ";", delete "and,".

Column 4, line 48, after "including" there should have been inserted -- a second manifold having --.

Column 4, line 48, after "means", "coupled" should have been -- and a second conduit coupling said second manifold --.

Column 4, line 50, after "fluid", there should have been inserted --, such as a clot dissolving enzyme, --.

Column 4, line 53, after "vein" there should have been inserted -- at the location of a clot therein; said tubular housing having a fluid-tight seal with an aperture extending therethrough disposed at the proximal end of said tubular housing; said second catheter extending through the aperture in the fluid-tight seal and through said tubular housing; and said second catheter also including a second fluid-tight seal having an aperture extending therethrough disposed at the proximal end of said second catheter for receiving a stylet therethrough --.

UNITED STATES PATENT AND TRADEMARK OFFICE
CERTIFICATE OF CORRECTION

PATENT NO. : 4,447,236
DATED : May 8, 1984 (page 3 of 3)
INVENTOR(S) : DAVID R. QUINN It is certified that error appears in the above-identified patent and that said Letters Patent is hereby corrected as shown below:

Column 6, line 1, after "second", delete "fluid delivery means each include an elongate".

Column 6, line 2, "manifold" should be -- manifolds --.

Column 6, line 2, "having" should be -- are elongate and each has --.

Column 6, line 3, after "coupling" there should have been inserted -- , --.

Column 6, line 4, "being" should have been -- are --.

Signed and Sealed this

Twentieth Day of November 1984

[SEAL]

Attest:

GERALD J. MOSSINGHOFF

Attesting Officer

Commissioner of Patents and Trademarks